(12) United States Patent
Marion

(10) Patent No.: US 8,247,561 B2
(45) Date of Patent: Aug. 21, 2012

(54) PREPARATION OF METHYLPENTAMETHYLENEDIAMINE AND METHYLPIPERIDINE

(75) Inventor: Philippe Marion, Vernaison (FR)

(73) Assignee: Rhodia Operations, Aubervilliers (FR)

( * ) Notice: Subject to any disclaimer, the term of this patent is extended or adjusted under 35 U.S.C. 154(b) by 0 days.

(21) Appl. No.: 12/934,465

(22) PCT Filed: Mar. 13, 2009

(86) PCT No.: PCT/EP2009/052966
§ 371 (c)(1),
(2), (4) Date: Oct. 29, 2010

(87) PCT Pub. No.: WO2009/121704
PCT Pub. Date: Oct. 8, 2009

(65) Prior Publication Data
US 2011/0034693 A1    Feb. 10, 2011

(30) Foreign Application Priority Data
Mar. 31, 2008  (FR) ...................................... 08 01750

(51) Int. Cl.
*C07D 211/12*   (2006.01)
*C07D 213/133*  (2006.01)
*C07C 209/48*   (2006.01)

(52) U.S. Cl. .......... 546/184; 546/252; 564/491
(58) Field of Classification Search .................. None
See application file for complete search history.

(56) References Cited

U.S. PATENT DOCUMENTS

| 4,248,799 | A | * | 2/1981  | Drake .............................. 564/491 |
| 4,521,602 | A | * | 6/1985  | Rebafka et al. ................ 546/184 |
| 4,755,604 | A | * | 7/1988  | Frank et al. .................... 546/184 |
| 4,885,391 | A | * | 12/1989 | Herkes .......................... 564/491 |

FOREIGN PATENT DOCUMENTS

WO  WO 2004/060833  7/2004

OTHER PUBLICATIONS

Anonymous, "Hydrogenation of Nitriles," *Research Disclosure*, Mar. 1, 1995, vol. 371, No. 12, Mason Publications, Hampshire, Great Britain.
International Search Report corresponding to PCT/EP 2009/052966.

* cited by examiner

*Primary Examiner* — Janet Andres
*Assistant Examiner* — Timothy R Rozof
(74) *Attorney, Agent, or Firm* — SNR Denton US LLP

(57) ABSTRACT

Methyl-2-pentamethylenediamine and methyl-3-piperidine are prepared by hydrogenation of methylglutaronitrile in the presence of a catalyst including cobalt, chromium, and nickel, especially a catalyst based on Raney cobalt doped with nickel and chromium.

13 Claims, No Drawings

PREPARATION OF METHYLPENTAMETHYLENEDIAMINE AND METHYLPIPERIDINE

CROSS-REFERENCE TO PRIOR APPLICATIONS

The present application is a U.S. National Phase Application of International Application No. PCT/EP2009/052966, filed Mar. 13, 2009, which claims the benefit of French Application No. 0801750, filed Mar. 31, 2008, both of which are hereby incorporated by reference in their entirety.

The present invention relates to a process for the manufacture of 2-methylpentamethylenediamine and of 3-methylpiperidine.

It relates to a process for the manufacture of 2-methylpentamethylenediamine and 3-methylpiperidine by hydrogenation of methylglutaronitrile.

Methylglutaronitrile is a compound obtained in conjunction with adiponitrile in the process for the hydrocyanation of butadiene. It is already known to convert this methylglutaronitrile to methylpentamethylenediamine (MPMD) by hydrogenation in the presence of various catalysts, such as Raney cobalt or Raney nickel. High degrees of conversion of methylglutaronitrile to MPMD have been obtained by using pure methylglutaronitrile and by carrying out the hydrogenation under high pressures, as is described in French patents 2 306 202 and 2 306 203.

A description has also been given of processes for the hydrogenation of methylglutaronitrile to give a mixture of 2-methylpentamethylenediamine (MPMD) and 3-methylpiperidine (MPP) with catalysts based on nickel or Raney nickel under high hydrogen pressures. Such processes have been described in particular in French patents 2 306 204, 2 306 205, 2 306 206, 2 306 207 and 2 306 208. The proportion of MPMD formed with respect to the MPP is variable, depending on the solvent and/or the catalyst used. As for the processes described above, these processes use a pure methylglutaronitrile (MGN) compound as starting material. A process for the hydrogenation of pure MGN to give MPMD and MPP in the presence of Raney cobalt doped with chromium has also been proposed by U.S. Pat. No. 4,885,391. This reaction is advantageously carried out in the presence of water. The degree of conversion of the MGN to give products of economic value, namely MPMD and MPP, is at most 85%, with formation of approximately 10% of heavy products not of economic value.

2-Methylpentamethylenediamine (MPMD) is used mainly in two applications, one as monomer for the manufacture of polyamide, in total or partial replacement of hexamethylenediamine, the other as starting material in the manufacture of β-picoline, which is itself a synthetic intermediate in manufacturing nicotinamide. This process is described in the literature, for example in the paper by S. Lanini and R. Prins published in Appl. Cat. A, 1996, 137, pp 287-306, under the title "Synthesis of 3-picoline from MGN over supported noble metals catalysts".

The proposal has also been made to synthesize β-picoline by dehydrogenation of a mixture of 2-methylpentamethylenediamine and 3-methylpiperidine, as described in U.S. Pat. No. 4,401,819.

Furthermore, methylglutaronitrile is mainly produced in the process for the manufacture of adiponitrile, a synthetic intermediate in the manufacture of hexamethylenediamine and caprolactam, which are important monomers in the production of polyamides.

Methylglutaronitrile is separated from adiponitrile by distillation and recovered in the form of a distillation fraction. In fact, the fraction recovered is a mixture of dinitrile compounds comprising predominantly methylglutaronitrile and a few percent of ethylsuccinonitrile and of adiponitrile.

An additional distillation is necessary in order to obtain pure methylglutaronitrile, a product used in the hydrogenation processes of the prior art. The tests described in U.S. Pat. No. 4,521,602 show that the conversion of MGN to 3-methylpyridine is obtained with a yield of 80% starting from pure MGN and only 42% with a mixture of dinitriles.

In addition, the processes for the conversion of MGN to MPMD and MPP described in the literature use high hydrogen pressures in order to obtain a percentage of conversion of MGN to MPMD+MPP of greater than 90%. Hydrogenation reaction is often carried out in the liquid medium.

In order to make it possible to lower the cost of manufacture of β-picoline, it is important to look for solutions which make it possible to carry out the conversion of MGN either in the pure form or present in the mixture of dinitriles with high yields for conversion of MGN to MPMD and MPP of greater than 90% and under milder operating conditions than those described in the prior art.

One of the aims of the present invention is to provide a process for the manufacture of 2-methylpentamethylenediamine and 3-methylpiperidine from pure methylglutaronitrile or methylglutaronitrile as a mixture with other nitriles with high degrees of conversion to MPMD+MPP, these two compounds being of economic value in downstream processes for the manufacture of important chemical compounds, such as β-picoline, as indicated above.

To this end, the invention provides a process for the manufacture of 2-methylpentamethylenediamine and 3-methylpiperidine by hydrogenation of methylglutaronitrile, characterized in that the hydrogenation is carried out in the presence of a catalyst comprising cobalt and, as doping elements, chromium and nickel at an absolute hydrogen pressure of less than 50 bar, preferably of less than 40 bar, advantageously of between 10 and 35 bar.

According to another characteristic of the invention, the hydrogenation is carried out in the presence of a solvent chosen from the group preferably consisting of alcohols, water or a mixture of these. It is also possible to use, as solvent, one of the compounds resulting from the hydrogenation reaction (MPMD and/or MPP), in combination with water.

Advantageously, the hydrogenation is carried out in the presence of a strong basic inorganic compound chosen from the group consisting of alkali metal hydroxides and ammonium hydroxide. Preferably, the basic compound is potassium hydroxide or aqueous ammonia.

The hydrogenation can be carried out at a temperature of between 60 and 160° C., advantageously between 80 and 140° C.

According to a novel characteristic of the invention, the catalyst comprises an amount of cobalt, expressed as elemental Co, of between approximately 85% and approximately 98% of the total weight of the catalyst, an amount of nickel, expressed as elemental Ni, of between approximately 0.1% and approximately 4% by weight of the catalyst and an amount of chromium, expressed as elemental Cr, of between approximately 0.1% and approximately 4% by weight of the catalyst.

According to a preferred characteristic of the invention, the cobalt present in the catalyst is a Raney cobalt.

The catalyst of the invention makes it possible to obtain a very high degree of conversion of MGN to MPMD and MPP of approximately 100% and thus to avoid the formation of a large amount of heavy compounds or compounds having a high boiling point, as was obtained with the catalysts of the state of the art.

In addition, according to another advantage of the process of the invention using a catalyst with a specific composition, it is possible to use, as starting material to be hydrogenated, a mixture of dinitriles comprising methylglutaronitrile, ethylsuccinonitrile and adiponitrile. This mixture of dinitriles advantageously corresponds to the distillation fraction produced in the process for the manufacture of adiponitrile by double hydrocyanation of butadiene, making it possible to separate the branched dinitriles (methylglutaronitrile, ethylsuccinonitrile) from adiponitrile.

This mixture of dinitriles generally has the following composition by weight:

| | |
|---|---|
| Methylglutaronitrile | of between 70% and 95% |
| Ethylsuccinonitrile | of between 5% and 30% |
| Adiponitrile | of between 0% and 10%. |

Thus, the process of the invention makes it possible to obtain a high degree of conversion of the MGN present in this mixture to give MPMD and MPP.

According to a preferred characteristic of the invention, the mixture of dinitriles can be enriched in methylglutaronitrile before feeding to the hydrogenation stage, for example by distillation.

2-Methylpentamethylenediamine, 3-methylpiperidine or their mixtures can be used as starting materials in the manufacture of β-picoline according to the processes described in the documents already mentioned above.

In the embodiment of the invention using a mixture of dinitriles as starting materials, it is possible to use the compounds resulting from the hydrogenation directly in the process for the manufacture of β-picoline, without separation and purification of the MPMD and MPP. However, it may be preferable to carry out a separation of these two compounds from the other products resulting from the hydrogenation of ESN or AdN. This separation can be carried out by any known technique and in particular distillation.

Other advantages and details of the invention will be illustrated by the examples given below solely by way of illustration.

Example 1 Comparative (Pure Mgn)

2 g of catalyst based on Raney nickel comprising 91% by weight of nickel and doped with 2% by weight of Cr are added to 100 g of a 20% by weight solution of MGN (99% purity) in ethanol and 1.5 g of $NH_3$ in the form of an aqueous $NH_4OH$ solution comprising 28% by weight of $NH_3$. The reactor is purged with nitrogen and then with hydrogen. The reaction medium is heated under hydrogen pressure and is stirred when the desired temperature is reached (100° C.). The reactor is cooled in order to keep the temperature of the medium at approximately 100° C. The relative pressure in the reactor is kept constant at a value of 25 bar. When the hydrogen is no longer being consumed, the mark of the end of the reaction, a sample of the reaction medium is withdrawn for analysis by gas chromatography.

The results of the analysis show that MGN is completely converted and that the selectivity for MPMD is 23% and that for MPP is 44%. The sum of the selectivities for products of economic value is thus 67%.

Example 2 of the Invention (Pure MGN)

2 g of catalyst based on Raney cobalt comprising 92% by weight of cobalt and doped with 2.2% by weight of Cr and 2.4% by weight of Ni are added to 100 g of a 20% by weight solution of MGN (99% purity) in ethanol and 1.5 g of $NH_3$ in the form of an aqueous $NH_4OH$ solution comprising 28% by weight of $NH_3$. The reactor is purged with nitrogen and then with hydrogen. The reaction medium is heated under hydrogen pressure and is stirred when the desired temperature is reached (100° C.). The reactor is cooled in order to keep the temperature of the medium at approximately 100° C. The pressure in the reactor is kept constant at a value of 25 bar. When the hydrogen is no longer being consumed, the mark of the end of the reaction, a sample of the reaction medium is withdrawn for analysis by gas chromatography.

The results of the analysis show that the MGN is completely converted and that the selectivity for MPMD is 80% and that for MPP is 20%. The sum of the selectivities for products of economic value is thus 100%.

The degree of conversion of the MGN to MPMD and MPP is notably higher than that obtained in example 1 with a catalyst based on Raney nickel but also than that shown in U.S. Pat. No. 4,885,391. Specifically, this document describes the hydrogenation of MGN to give MPMD and MPP in the presence of a chromium-doped Raney cobalt catalyst. The maximum degree of conversion is of the order of 80 to 85% with the formation of compounds of high boiling point representing approximately 10% of the products obtained.

Example 3 Comparative (Mixture of Dinitriles)

2 g of catalyst based on Raney nickel comprising 91% by weight of nickel and doped with 2% by weight of Cr are added to 100 g of a 20% by weight solution in ethanol of a mixture of dinitriles, referred to as crude MGN, comprising:
  86.9% by weight of methylglutaronitrile
  11.2% by weight of ethylsuccinonitrile
  1.9% by weight of adiponitrile
and 1.5 g of $NH_3$ in the form of an aqueous $NH_4OH$ solution comprising 28% by weight of $NH_3$. The reactor is purged with nitrogen and then with hydrogen. The reaction medium is heated under hydrogen pressure and is stirred when the desired temperature is reached (100° C.). The reactor is cooled in order to keep the temperature of the medium at approximately 100° C. The pressure in the reactor is kept constant at a value of 25 bar. When the hydrogen is no longer being consumed, the mark of the end of the reaction, a sample of the reaction medium is withdrawn for analysis by gas chromatography.

The results of analysis show that the conversion of the MGN is 99.9% and the selectivity for MPMD is 22% and that for MPP is 37%. The sum of the selectivities for products of economic value is thus 59%.

Example 4 of the Invention (Mixture of Dinitriles)

2 g of catalyst based on Raney cobalt comprising 92% by weight of cobalt and doped with 2.2% by weight of Cr and 2.4% by weight of Ni are added to 100 g of a 20% by weight solution in ethanol of a mixture of dinitriles, referred to as crude MGN, comprising:
  86.9% by weight of methylglutaronitrile
  11.2% by weight of ethylsuccinonitrile
  1.9% by weight of adiponitrile and 1.5 g of NH$_3$ in the form of an aqueous NH$_4$OH solution comprising 28% by weight of NH$_3$. The reactor is purged with nitrogen and then with hydrogen. The reaction medium is heated under hydrogen pressure and is stirred when the desired temperature is reached (100° C.). The reactor is cooled in order to keep the temperature of the medium at approximately 100° C. The pressure in the reactor is kept constant at a value of 25 bar. When the hydrogen is no longer being consumed, the mark of the end of the reaction, a sample of the reaction medium is withdrawn for analysis by gas chromatography.

The results of the analysis show that the MGN is completely converted and the selectivity for MPMD is 58% and that for MPP is 31%. The sum of the selectivities for products of economic value is thus 89%.

Example 5 of the Invention (Mixture of Dinitriles)

2 g of catalyst based on Raney cobalt comprising 92% by weight of cobalt and doped with 2.2% by weight of Cr and 2.4% by weight of Ni are added to 100 g of a 20% by weight solution in ethanol of a mixture of dinitriles, referred to as crude MGN, comprising:
- 86.9% by weight of methylglutaronitrile
- 11.2% by weight of ethylsuccinonitrile
- 1.9% by weight of adiponitrile and 1.5 g of NH$_3$ in the form of an aqueous NH$_4$OH solution comprising 28% by weight of NH$_3$. The reactor is purged with nitrogen and then with hydrogen. The reaction medium is heated under hydrogen pressure and is stirred when the desired temperature is reached (140° C.). The reactor is cooled in order to keep the temperature of the medium at approximately 140° C. The pressure in the reactor is kept constant at a value of 25 bar. When the hydrogen is no longer being consumed, the mark of the end of the reaction, a sample of the reaction medium is withdrawn for analysis by gas chromatography.

The results of the analysis show that the MGN is completely converted and the selectivity for MPMD is 64% and that for MPP is 28%. The sum of the selectivities for products of economic value is thus 92%.

Example 6 of the Invention (Mixture of Dinitriles)

2 g of catalyst based on Raney cobalt comprising 92% by weight of cobalt and doped with 2.2% by weight of Cr and 2.4% by weight of Ni are added to 100 g of a 20% by weight solution, in an MPP (3-methylpiperidine)/water 95/5 (parts by weight) mixture, of a mixture of dinitriles, referred to as crude MGN, comprising:
- 86.9% by weight of methylglutaronitrile
- 11.2% by weight of ethylsuccinonitrile
- 1.9% by weight of adiponitrile and 1.5 g of NH$_3$ in the form of an aqueous NH$_4$OH solution comprising 28% by weight of NH$_3$. The reactor is purged with nitrogen and then with hydrogen. The reaction medium is heated under hydrogen pressure and is stirred when the desired temperature is reached (100° C.). The reactor is cooled in order to keep the temperature of the medium at approximately 100° C. The pressure in the reactor is kept constant at a value of 25 bar. When the hydrogen is no longer being consumed, the mark of the end of the reaction, a sample of the reaction medium is withdrawn for analysis by gas chromatography.

The results of the analysis show that the MGN is completely converted and the selectivity for MPMD is 49% and that for MPP is 19%. The sum of the selectivities for products of economic value is thus 68%.

Example 7 Comparative (Mixture of Dinitriles)

2 g of catalyst based on Raney nickel comprising 91% by weight of nickel and doped with 2% by weight of Cr are added to 100 g of a 20% by weight solution, in an MPP (3-methylpiperidine)/water 95/5 (parts by weight) mixture, of a mixture of dinitriles, referred to as crude MGN, comprising:
- 86.9% by weight of methylglutaronitrile
- 11.2% by weight of ethylsuccinonitrile
- 1.9% by weight of adiponitrile and 1.5 g of NH$_3$ in the form of an aqueous NH$_4$OH solution comprising 28% by weight of NH$_3$. The reactor is purged with nitrogen and then with hydrogen. The reaction medium is heated under hydrogen pressure and is stirred when the desired temperature is reached (100° C.). The reactor is cooled in order to keep the temperature of the medium at approximately 100° C. The pressure in the reactor is kept constant at a value of 25 bar. When the hydrogen is no longer being consumed, the mark of the end of the reaction, a sample of the reaction medium is withdrawn for analysis by gas chromatography.

The results of the analysis show that the MGN is completely converted and the selectivity for MPMD is 20% and that for MPP is 13%. The sum of the selectivities for products of economic value is thus 33%.

What is claimed is:

1. A process for the preparation of 2-methylpentamethylenediamine and 3-methylpiperidine, comprising hydrogenating methylglutaronitrile in the presence of a catalyst which comprises cobalt doped with nickel and chromium, under an absolute hydrogen pressure of less than 50 bar.

2. The process as defined by claim 1, wherein the hydrogenation reaction is carried out under an absolute hydrogen pressure ranging from 10 to 35 bar.

3. The process as defined by claim 1, wherein the hydrogenation is carried out in the presence of a solvent selected from the group consisting of alcohols, water or mixture thereof.

4. The process as defined by claim 1, wherein the hydrogenation is carried out in the presence of a strong basic inorganic compound selected from the group consisting of alkali metal hydroxides and ammonium hydroxide.

5. The process as defined by claim 1, wherein the hydrogenation is carried out at a temperature ranging from 60 to 160° C.

6. The process as defined by claim 1, wherein the percentage by weight of cobalt in the catalyst, expressed as Co, ranges from 85% to 98%, with respect to the weight of catalyst.

7. The process as defined by claim 1, wherein the percentage by weight of nickel in the catalyst, expressed as Ni, ranges from 0.1% to 4%, with respect to the weight of catalyst.

8. The process as defined by claim 1, wherein the percentage by weight of chromium in the catalyst, expressed as Cr, ranges from 0.1% to 4%, with respect to the weight of catalyst.

9. The process as defined by claim 1, wherein the cobalt present in the catalyst comprises a Raney cobalt.

10. A process for the synthesis of β-picoline, comprising dehydrogenating the mixture of 2-methylpentamethylenediamine and 3-methylpiperidine prepared according to the process as defined in claim 1.

11. A process for the preparation of 2-methylpentamethylenediamine and 3-methylpiperidine, comprising hydrogenating a mixture of dinitriles comprising methylglutaronitrile, ethylsuccinonitrile and adiponitrile, in the presence of a catalyst which comprises cobalt doped with nickel and chromium, under an absolute hydrogen pressure of less than 50 bar.

12. The process as defined by claim 11, wherein the mixture of dinitriles has the following composition by weight:
Methylglutaronitrile ranging from 70% to 95%
Ethylsuccinonitrile ranging from 5% to 30%
Adiponitrile ranging from 0% to 10%.

13. The process as defined by claim 11, wherein the mixture of dinitriles is enriched in methylglutaronitrile prior to the hydrogenation stage.

* * * * *